United States Patent
Hubert et al.

(10) Patent No.: US 7,227,165 B2
(45) Date of Patent: Jun. 5, 2007

(54) SYSTEM AND METHOD FOR CLASSIFICATION OF TIMBER

(75) Inventors: Yvon Hubert, Mirabel (CA); Martin Castonguay, Blainville (CA)

(73) Assignee: Comact Optimisation Inc., Boisbriand, QC (CA)

( * ) Notice: Subject to any disclaimer, the term of this patent is extended or adjusted under 35 U.S.C. 154(b) by 151 days.

(21) Appl. No.: 10/391,773

(22) Filed: Mar. 20, 2003

(65) Prior Publication Data

US 2003/0178586 A1  Sep. 25, 2003

(30) Foreign Application Priority Data

Mar. 20, 2002  (CA) ................................ 2378625

(51) Int. Cl.
*G01V 8/00* (2006.01)
(52) U.S. Cl. ............... 250/559.25; 83/365; 250/559.24
(58) Field of Classification Search ...............
250/559.22–59.27, 223 R, 208.1; 144/357;
356/237.1, 430; 83/365
See application file for complete search history.

(56) References Cited

U.S. PATENT DOCUMENTS

| | | | | |
|---|---|---|---|---|
| 3,187,185 A | * | 6/1965 | Milnes ..................... | 250/222.1 |
| 3,802,774 A | * | 4/1974 | Eschler et al. ............. | 356/637 |
| 4,149,089 A | * | 4/1979 | Idelsohn et al. ........ | 250/559.42 |
| 4,221,974 A | * | 9/1980 | Mueller et al. ........ | 250/559.48 |
| 4,541,722 A | * | 9/1985 | Jenks .......................... | 356/606 |
| 4,803,371 A | | 2/1989 | Durland ................... | 250/559.2 |
| 5,056,922 A | * | 10/1991 | Cielo et al. ................. | 356/604 |
| 5,412,220 A | * | 5/1995 | Moore .................... | 250/559.48 |
| 5,960,104 A | * | 9/1999 | Conners et al. ............. | 382/141 |
| 6,618,155 B2 | * | 9/2003 | Metcalfe et al. ............ | 356/625 |
| 6,757,058 B1 | * | 6/2004 | Carman et al. .......... | 356/237.2 |
| 6,825,936 B2 | * | 11/2004 | Metcalfe et al. ............ | 356/602 |

FOREIGN PATENT DOCUMENTS

CA  2111950  9/1994

* cited by examiner

*Primary Examiner*—Thanh X. Luu
*Assistant Examiner*—Stephen Yam
(74) *Attorney, Agent, or Firm*—Nixon & Vanderhye

(57) ABSTRACT

The present invention provides a system and a method to grade a piece of wood and simultaneously to classify this piece of wood by allowing an examination of four longitudinal faces thereof, so as to determine optimal specifications for a subsequent use thereof such as shaving, trimming ends, and other applications. The system comprises a structure, a transversal conveyor, a vision unit and a processing unit. The vision unit is partly located above the conveyor in an inclined plane, collecting data on a lateral and upper longitudinal face of an object as the object moves with the conveyor, and partly located under the conveyor, at an angle therewith, collecting data from a complementary lateral longitudinal face of the object as well as from an inferior longitudinal face thereof, as the object moves with the conveyor. The system allows classification of wooden pieces according to predetermined standards, at a rate of 200 pieces per minute with a margin of error less than or equal to 2%.

22 Claims, 5 Drawing Sheets

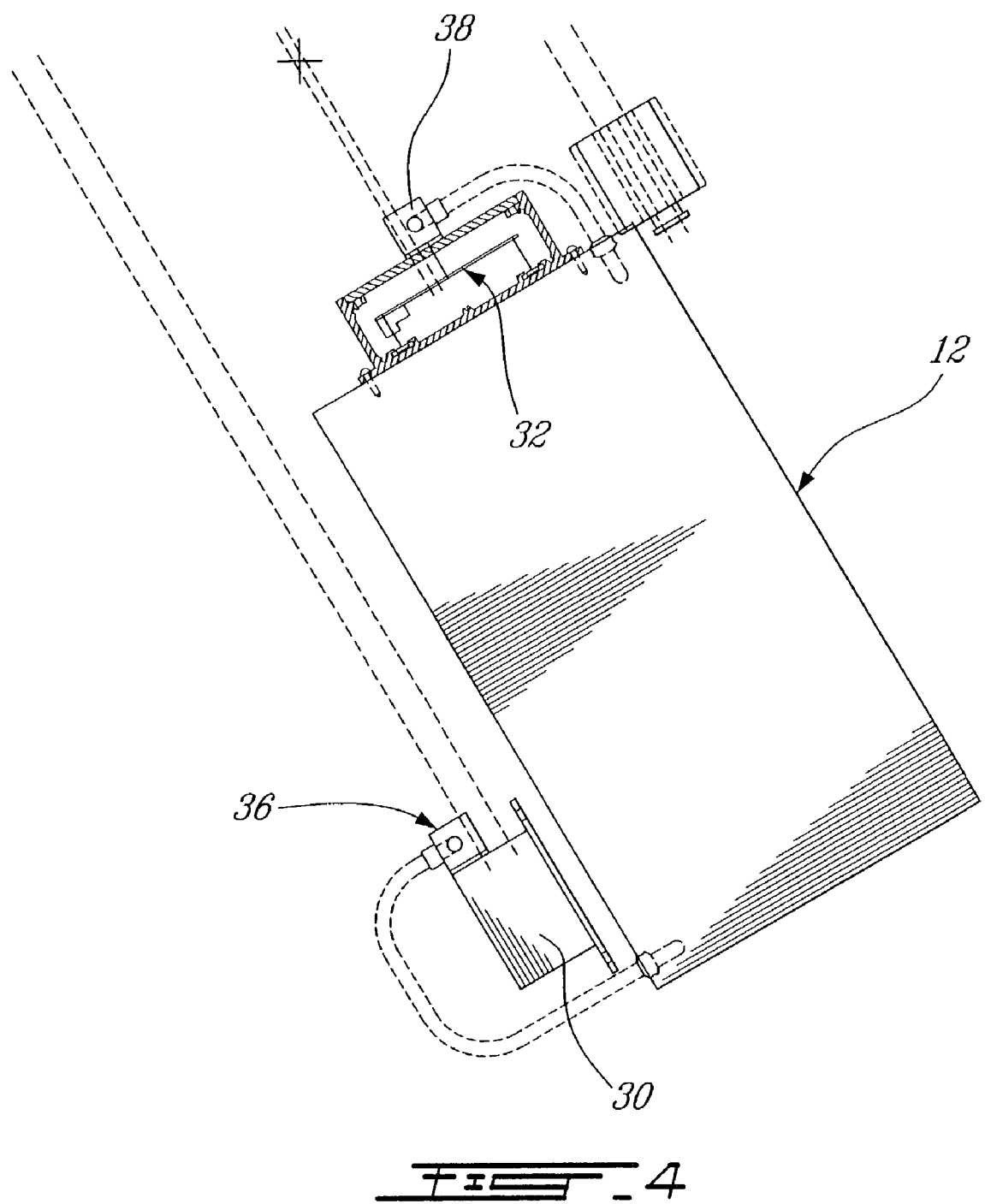

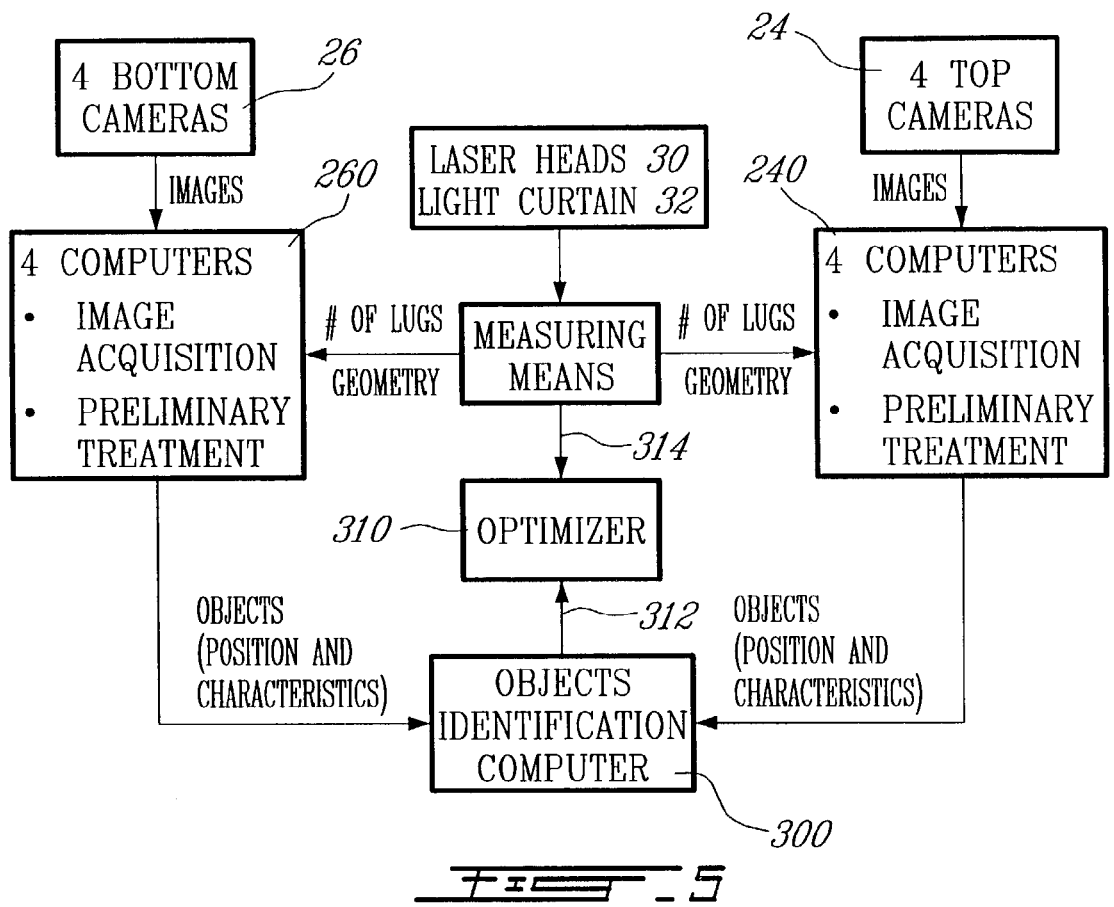
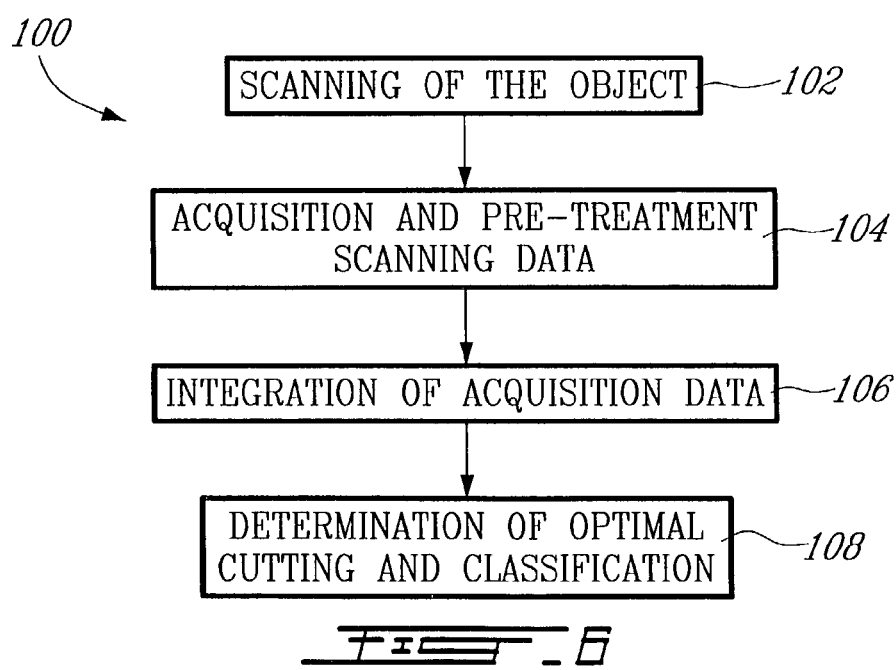

SYSTEM AND METHOD FOR CLASSIFICATION OF TIMBER

FIELD OF THE INVENTION

The present invention relates to objet identification and classification. More specifically, the present invention is concerned with a method and a system for classifying three-dimensional objects.

BACKGROUND OF THE INVENTION

In the wood processing industry for example, wood grading and wood classification is an important step to sort out a variety of wood grades in accordance with specific applications.

Traditionally, grading of planed lumbers is done by a qualified operator. The operator examines and segregates the wood pieces according to a numeric grade such as grade 1, grade 2, and grade 3 following predetermined standards. This evaluation must be done very rapidly, generally at a rate of sixty pieces per minute per operator, according to several criteria and in adherence to stringent rules. Grading allows selecting and dispatching wood pieces according to the specific applications and to a client's needs, thereby allowing rationalizing the use of wood in a cost-effective way.

Typically, classification is done according to norms generated by national commissions with the purpose of obtaining uniform characteristics and quality throughout plants manufacturing a given type of wood. The current norms allow a maximum variation between graders of 5% of "under-classification".

Obviously, the operators work under tremendous pressure. Moreover, evaluation standards used by the operators are so strict that they result in "over-quality", meaning that approximately 15% of the wood pieces are over-classified, i.e. graded in an inferior grade, which in turn results in reduced profits. Furthermore, since automation efforts have increased the manufacturing rates up to 200 wood pieces per minute, classification by operators at a maximum rate of 60 pieces per minute constitutes a major bottleneck.

A number of technologies have been developed to automate the classification work. However, few have been successful in increasing the rate of classification and allowing reducing human intervention while maintaining the desired quality.

Indeed, a number of attempts have been made to simplify and accelerate wood classification. Since evaluation of an object requires that a peripheral surface thereof is evaluated, it has been contemplated positioning cameras above and under a conveyor carrying the wood pieces for example, but a recurrent problem is the accumulation of debris on lower cameras. In U.S. Pat. No. 5,412,220 issued to Moore in 1995, this problem is addressed by adding to the conveyor a mechanism to rotate each wood piece in such a way that all four longitudinal faces thereof can be exposed to a camera.

In spite of such developments, there is still a need for a system and a method for evaluating and classifying objects such as lumber planks or timbers and wood pieces for example, for subsequent treatment, which allow quality and speed at a reasonable price and with an increased performance.

OBJECTS OF THE INVENTION

An object of the present invention is therefore to provide an improved system and a method for classification of timber.

SUMMARY OF THE INVENTION

More specifically, in accordance with the present invention, there is provided a system for classification of an object, comprising: a structural body; a conveyor supported by the structural body and carrying the object; and a vision unit related to the structural body and inclined at an angle relatively to a movement axis of the conveyor; wherein the vision unit collects data on the object on four longitudinal faces thereof and on a periphery thereof including thickness, width, length, shape and defects thereof.

Moreover, there is provided a grade optimizer for lumber planks comprising a structural body, a transversal conveyor, a vision unit comprising a plurality of cameras, and a processing unit; wherein the structural body supports the transversal conveyor, the vision unit and the processing unit; the transversal conveyor transporting the lumber planks; the vision system comprising a first vision sub-unit positioned above and at a first predetermined angle relative to a movement axis of the transversal conveyor; a second vision sub-unit placed below and at second predetermined angle relative to the movement axis of the transversal conveyor.

Furthermore, there is provided a method for classification of a three-dimensional object moved by a conveyor comprising: providing a first vision unit positioned above the conveyor at a first angle relatively to a movement axis of the conveyor; providing a second vision unit positioned under the conveyor at a second angle relatively to the movement axis of the conveyor; providing a measuring means connected to the first and to the second vision units; and acquiring and processing data obtained by the measuring means.

Other objects, advantages and features of the present invention will become more apparent upon reading of the following non-restrictive description of embodiments thereof, given by way of example only with reference to the accompanying drawings.

BRIEF DESCRIPTION OF THE DRAWINGS

In the appended drawings:

FIG. 3 is a simplified side view of a vision unit comprised in the system of FIG. 1;

FIG. 4 is a sectional view of a cleaning means of the vision unit of FIG. 3;

FIG. 6 is a flowchart of a method making use of the system of FIG. 1 according to an embodiment of a second aspect of the present invention.

DESCRIPTION OF EMBODIMENTS OF THE INVENTION

Generally stated, the present invention provides a system and a method for classification of three-dimensional objects, such as wood pieces, according to quality and/or use, allowing an analysis of the shape and surface defects.

Figure 1:
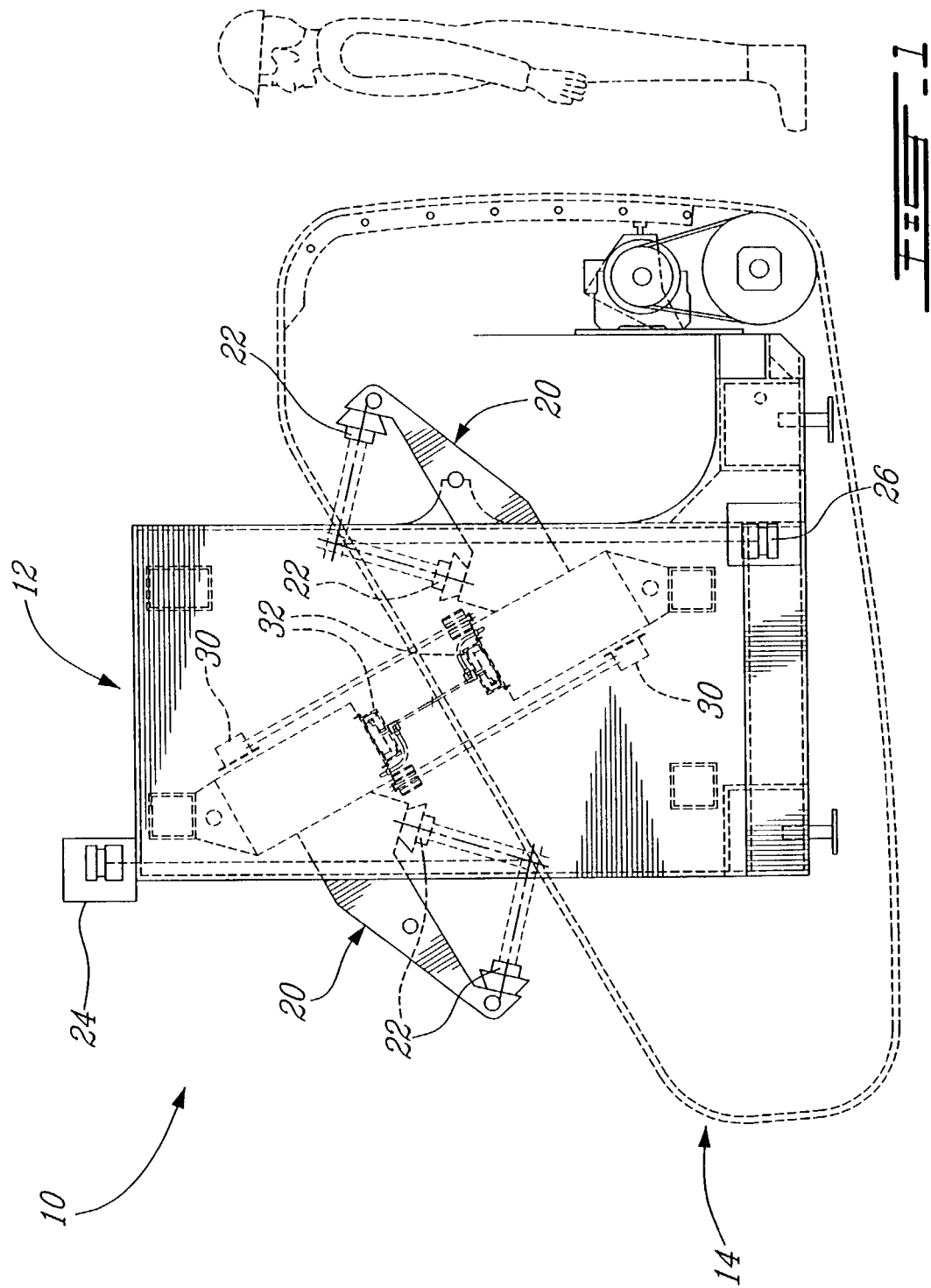
FIG. 1 is a general side view of a system according to an embodiment of a first aspect of the present invention.
Figure 2:
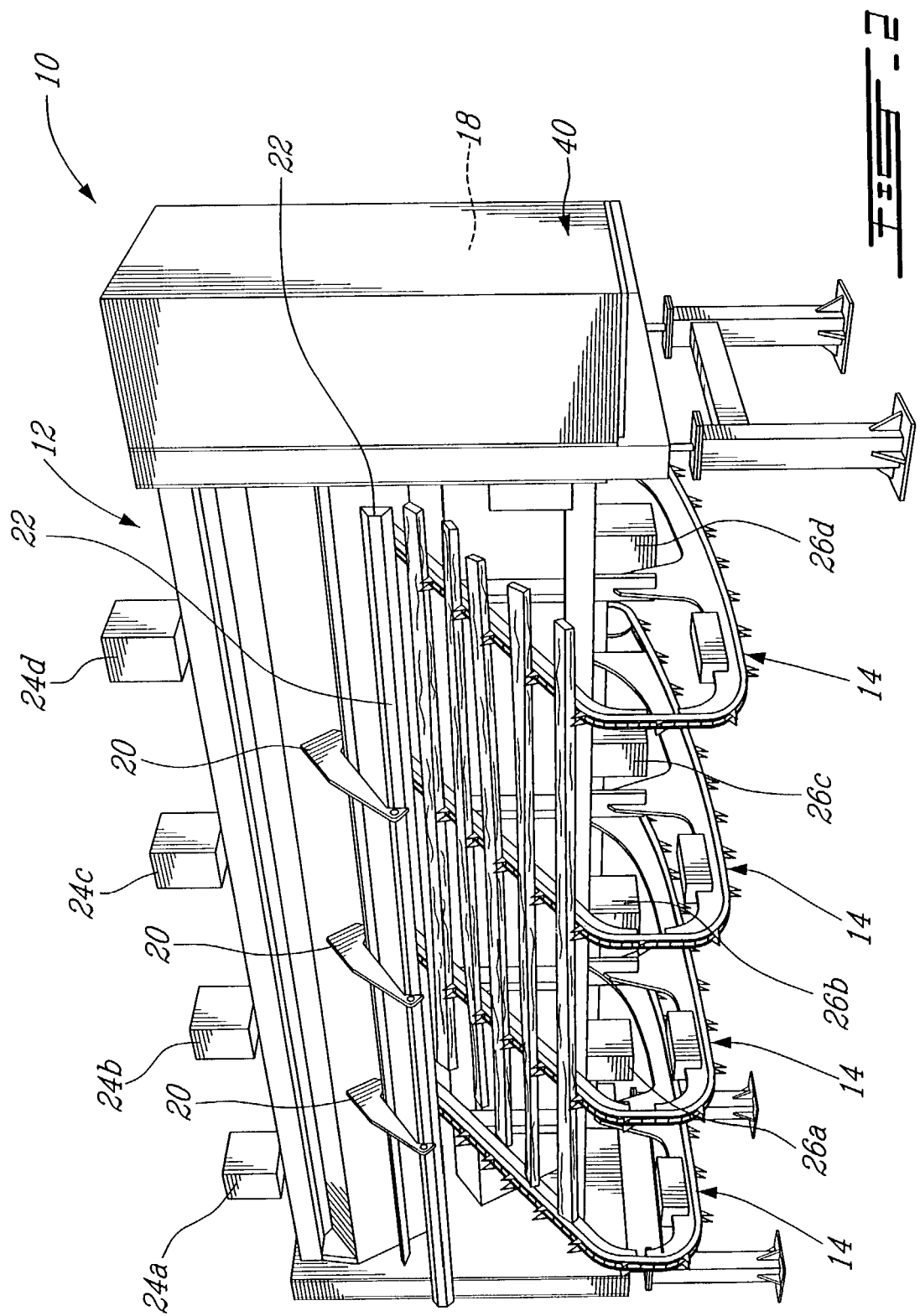
FIG. 2 is a perspective view of the system of FIG. 1.

Turning first to FIGS. 1–3 of the appended drawings, a system according to an embodiment of the present invention will now be described. The system 10 generally comprises a frame 12; a conveyor unit 14; a vision unit 16; and a processing unit 18.

The frame 12 is a robust structural body, generally metallic, which supports the conveyor unit 14 conveying objects. The structural body 12 may be provided with articulated arms 20 extending and adjusting according to different angles.

The conveyor unit 14 comprises a transversal conveyor supporting an object to be analyzed with a minimum of contact points. Object transportation on the conveyor unit 14 is performed with a minimum of attachment means by adjusting the inclination slope of the conveyor unit 14 relative to the horizontal, taking advantage of the fact that the conveyor unit 14 is adjustable according to three reference axis. For example, an inclination of approximately 30°±15 was used in the described embodiment. It is to be noted that the conveyor unit 14 is also adjustable in length.

The vision unit 16 comprise lights 22 that may be supported by the articulated arms 20, and a number of mobile and adjustable vision sub-units as will be further described hereinbelow. The vision unit 16 may be separate and remotely located from the frame 12.

As illustrated in FIGS. 1 and 3, the vision unit 16 comprise a plurality of independent cameras 24, 26, which may be anchored permanently on the frame 12 and assembled in two sub-units: a first sub-unit (24a–24d) is positioned above the conveyor unit 14 and a second sub-unit (26a–26d) is positioned below the conveyor unit 14. The independent cameras 24, 26 may be color high-speed high-resolution cameras.

The plurality of cameras 24a–24d and 26a–26d of each sub-unit is placed in a row transversally with regard to the frame 12, in such a way that the cameras of a same sub-unit read simultaneously a distinct part of an object to be examined in such a way that the resulting collected data as a whole correspond to two longitudinal faces of the object. The vision axis of each camera is inclined relatively to the conveyor movement axis to allow that each camera can read two longitudinal faces of the object to be analyzed as it is being moved by the conveyor unit 14. The cameras are connected to computers of the processing unit 18, as will be detailed hereinbelow.

The vision unit 16 may further comprise additional vision sub-units to collect data on transversal ends of the object to be analyzed.

The lights 22 of the vision unit 16 allow an optimal data reading. The vision unit 16 may further comprise measurement means including laser heads 30, allowing cross-section readings of thickness and shape, and a light curtain 32, so that as the object passes between an emitter and a receiver of the light curtain 32, its length and width are measured.

Automatic cleaning means comprising air nozzles 36, 38 (see) may be also provided and activated to trigger an automatic cleaning of the different parts (laser heads 30, light curtain 32) of the measurement means of the vision system 16, to eliminate debris such as dust and wood chips for instance.

In a specific embodiment given by way of example for clarification purpose, the vision unit 16 is inclined at an angle relatively to the movement axis of the conveyor 14 unit and comprises eight linear high speed colour high resolution cameras 24, 26 divided into two vision sub-units located above and under the conveyor unit 14 respectively. The first vision sub-unit comprises a set of four cameras 24a–24d located in a row and distributed at regular intervals on the frame 12 along a transversal axis (see FIG. 3). This sub-unit is located at angle of approximately 60°±15 above the conveyor unit 14 to collect data from an upper and a right lateral longitudinal sides of the object to be analyzed.

The second vision sub-unit (not shown in FIG. 3) correspondingly comprises a set of four cameras 26a–26d arranged in a row and similarly distributed on the frame 12 along the same transversal axis. Located at an angle of approximately 120°±15 under the conveyor unit 14, the second vision sub-unit 26a–26d is used to collect data from a lower and a left lateral longitudinal sides of the object on the conveyor unit 14.

Such a spatial configuration of the vision system 16 allows to collect data on two longitudinal sides of the object to be analyzed with a single vision system, by allowing each vision sub-unit to collect data on two longitudinal sides while reducing by half the number of required cameras.

The processing unit 18 comprises a master computer, a plurality of independent high speed computers linked to the cameras 24 and 26, a module dedicated to shape and object identification (not shown), and an optimization computer. The processing unit 18 may monitor the location of the vision unit 16 and/or of the vision sub-units as well as the inclination of the adjustable conveyor unit 14 as parameters; these data may be inputted either manually or automatically. In the embodiment illustrated in FIG. 2, the processing unit 18 is sheltered in a chamber 40 provided in the frame 12. Obviously, the processing unit 18 may alternatively be separately or remotely located from the frame 12.

It should now be apparent that the vision unit 16 allows a precise measurement of the shape and appearance of an object, such as a wood piece for example, on four longitudinal faces thereof and/or on a periphery thereof, by collecting data measurements including the thickness, the width, the length and the shape of the object. Furthermore, the vision unit 16 allows to detect a number of defects, including solid knots, embedded knots, resin pockets, blue stain, red stain, cavities, bark pockets, splits, warp, worm holes, etc in a wood piece for example. The data collected by the cameras 24, 26 of the vision sub-units located over and under the conveyor unit 14 respectively, as well as data collected by the measurement means, are transmitted to the processing unit 18 for treatment by the optimization software, which combines all available collected measurements to yield an optimal cut solution and grading of each wood piece.

It is to be noted that the present system allows handling 3D objects of a variety of shape and geometry. In particular, the system may be adapted to a range of longitudinal wood pieces of different lengths and types (for example, rough, raw, planed or uncut) by obvious adjustment of the vision unit 16.

As people in the art will appreciate, the system of the present invention provides a spatial optimized configuration of functional units, by allowing a transversal conveyor unit to dispatch objects and by separating the vision unit into sub-units comprising for example a first vision sub-unit located above the conveyer unit and a second vision sub-unit located under the conveyor unit.

This spatial configuration has several advantages, including the following. First, the transversal movement of the objects with the conveyor combined to the transversal position of the cameras allows high processing rates. In particular, the system 10 is able to read data at a rate exceeding 200 wood pieces per minute. Second, the inclination of the cameras relatively to the movement of the conveyor allows the system to read a plurality of faces of the object by using only a limited number of computers and cameras, which results in reduced overall costs. Indeed, the configuration described hereinabove provides that the upper vision sub-unit reads data on the superior periphery of the object while, simultaneously, the lower vision sub-unit can read data on the lower periphery of the object. Thirdly, the system, being provided with a transversal conveyor, requires less space than would an equivalent system equipped with a longitudinal conveyor. The slope of the conveyor also contributes to reduce the required space. Finally, cleaning means of the vision unit permits an efficient use of cameras located under the conveyor unit, since it takes care of dust and wood chips that are often causes obstruction of vision units used in the wood processing industry for example.

The spatial configuration of the vision unit combined with an adapted processing unit therefore allows the system of the present invention to reach high rates of the order of 200 pieces per minute or higher, with precision in a efficient way, allowing for example classification of wood pieces with less than 2% of over-classification. Indeed, such a configuration allows to analyze, classify and find the optimal cutting solutions for lumber planks with a length of 16 to 24 feet for example, with a speed reaching more than 200 boards/minute with a margin of error of 2%.

Figure 5:
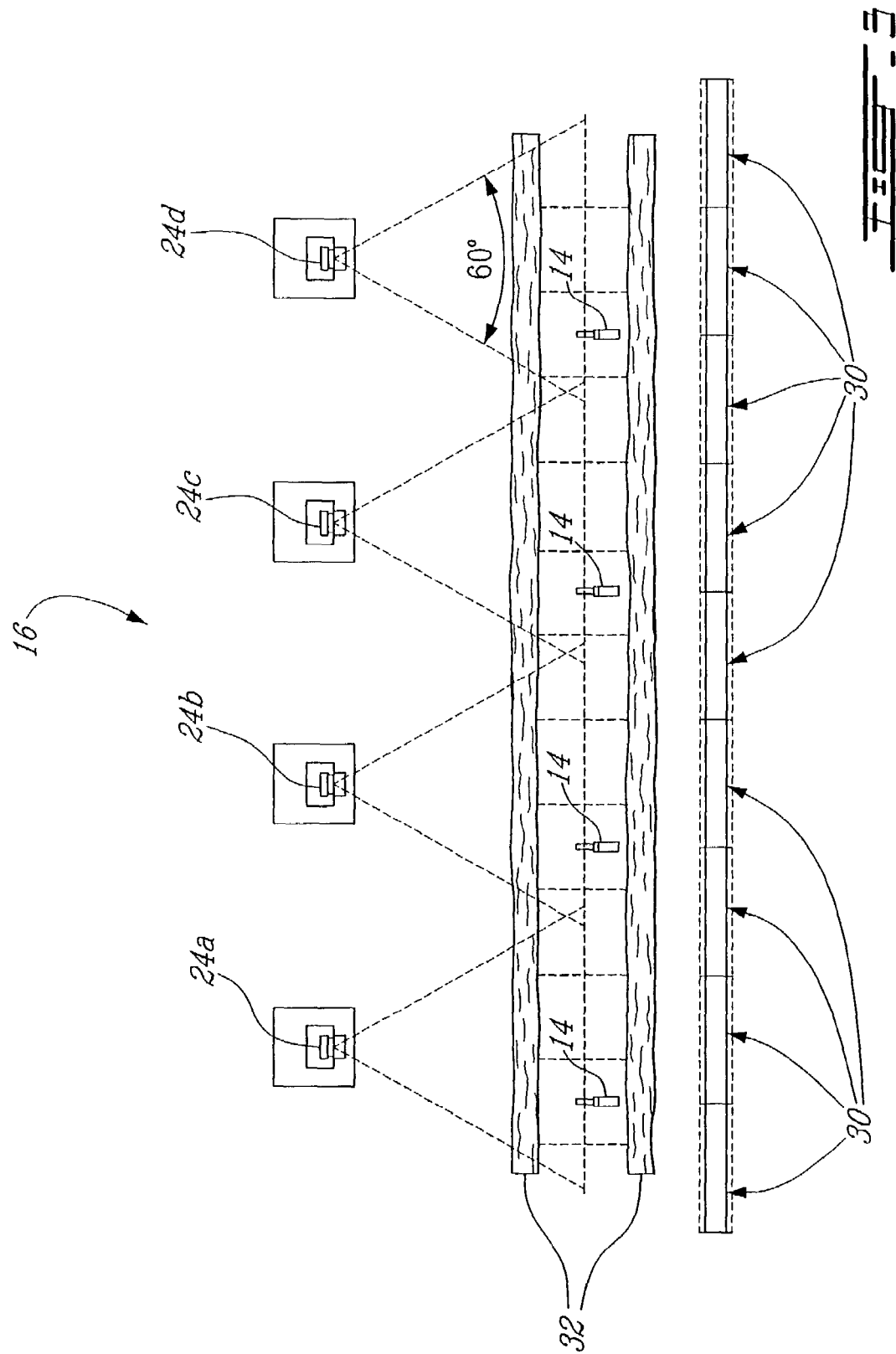
FIG. 5 is a flowchart of operation of a processing unit comprised in the system of FIG. 1.

Turning now to FIGS. 5–6 of the appended drawings, a method according to a second aspect of the present invention in relation to the system described hereinabove will now be described.

Generally, the processing unit 18 comprises a master component to control and monitor operation parameters of the system; at least one component linked directly to the vision unit 16 and dedicated to an acquisition and preliminary treatment of images of the object; a component integrating all data collected relatively to the object including defects and position thereof; and a component computing an optimal solution for the object.

According to a possible embodiment, the processing unit 18 comprises a number of high-speed independent computers. Computers 240, 260, linked to the top and bottom cameras 24 and 26, respectively are dedicated to the acquisition and the preliminary treatment of images of an object to be analyzed. A computer 300 linked to the computers 240, 260 integrates the data relative to the object including defects and location thereof.

The defect identification and positioning (312) is transmitted to a computer 310, together with data 314 collected by the measuring means of the vision unit 16 and including a geometrical shape of the object. The computer 310 that includes a grade optimizer expert system that determines for each object an optimal cutting solution, in the case of wood pieces particularly.

Classification decisions and optimal cutting solutions are then transferred to a programmable control unit (not shown), for execution of the corresponding cutting and sorting.

FIG. 6 is a flowchart of the main steps of the method. The method 100 comprises scanning of an object to be analyzed (102); acquisition and pre-treatment of scanning data (104); integration of acquisition data (106); and determination of optimal cutting and classification (108).

The scanning of the object in step 102 is done by cameras and comprises determining the geometrical shape thereof.

Pre-treatment of scanning data in step 104 may be performed by computers connected to the cameras used in step 102 and comprises filtration of the scanned images and preliminary recognition of suspicious zones on these images. Acquisition and pre-treatment allow the identification of the object.

Integration of acquisition data (106) and determination of optimal cutting and classification (108) is performed by a processing unit as described hereinabove.

From the foregoing, people in the art will appreciate that the system and the method of the present invention facilitates data collection on the four longitudinal faces of an object to evaluate with a minimum of equipment ingeniously configured in the available space, and allows classification of wood pieces in grades with a high precision level, a low error margin and a rate of evaluation comparable to other automated systems in the wood transformation, with a high rate of pieces inspected per minute. Obviously, the system may be a grade optimizer for lumber planks.

Although the present invention has been described hereinabove by way of embodiments thereof, it can be modified, without departing from the spirit and nature of the subject invention as defined in the appended claims.

What is claimed is:

1. A system for classification of an object, comprising:
   a frame;
   a transversal conveyor supported by said frame and carrying the object along a direction perpendicular to a lengthwise direction thereof, said transversal conveyor having an inclination relative to a horizontal direction; and
   vision subunits placed transversely with regard to said frame, inclined at an angle relatively to a movement axis of said transversal conveyor, said vision subunits comprising measuring means and cleaning means;
   wherein said vision subunits scan two sides and two edges of the object.

2. A system for classification of an object, comprising:
   a frame;
   a transversal conveyor supported by said frame and carrying the object along a direction perpendicular to a lengthwise direction thereof, said transversal conveyor having an inclination relative to a horizontal direction;
   vision subunits placed transversely with regard to said frame, inclined at an angle relatively to a movement axis of said transversal conveyor; said vision subunits scanning two sides and two edges of the object; and
   a processing unit;
   wherein said processing unit comprises a master component to control and monitor operation parameters of the system; at least one component linked directly to the vision subunits and dedicated to an acquisition and preliminary treatment of images of the object; a component integrating all data collected relatively to the object including defects and position thereof; a component computing an optimal solution for the object.

3. A system for classification of an object, comprising:
   a frame;
   a transversal conveyor supported by said frame and carrying the object along a direction perpendicular to a lengthwise direction thereof, said transversal conveyor having an inclination relative to a horizontal direction; and
   vision subunits placed transversely with regard to said frame, inclined at an angle relatively to a movement axis of said transversal conveyor; said vision subunits scanning two sides and two does of the object;
   wherein said frame comprises articulated arms extending and adjusting according to different angles for supporting lights of said vision subunits.

4. The system according to any one of claims 1, 2 and 3, wherein said vision subunits comprise a first vision sub-unit comprising at least one camera placed above said transversal conveyor at a first angle between an axis of said at least one camera and the movement axis of said transversal conveyor so as to scan a first side and a first edge of the object; a second vision sub-unit comprising at least one camera placed under said transversal conveyor at such a second angle between the at least one camera vision axis and the transversal conveyor movement axis so as to scan a second side and a second edge of the object.

5. The system according to claim 4, wherein said first angle is approximately 60±15 degrees and said second angle is approximately 120±15 degrees.

6. The system according to any one of claims 1, 2 and 3, wherein said vision subunits comprise a plurality of high-speed color linear cameras anchored permanently on said frame.

7. The system according to any one of claims 1 and 3, further comprising a processing unit.

8. The system according to claim 2, wherein said processing unit includes an expert system.

9. The system according to any one of claims 1, 2 and 3, further comprising additional vision sub-units to collect data on transversal ends of the object.

10. The system according to any one of claims 1, 2 and 3, wherein the inclination of the transversal conveyor relative to the horizontal direction is of approximately 30±15 degrees.

11. The system according to claim 2, wherein said processing unit integrates a location of said vision subunits and the inclination of said transversal conveyor unit as parameters.

12. The system according to any one of claims 1, 2 and 3, wherein the object comprises three-dimensional longitudinal pieces.

13. The system according to any one of claims 1, 2 and 3, wherein the system is a grade classification system for wood pieces.

14. A grade optimizer for lumber planks comprising a frame supporting a transversal conveyor, a vision unit comprising a plurality of cameras and cleaning means, and a processing unit; wherein said cameras are placed in rows transversally with regard to said frame; said transversal conveyor having an inclination angle and transporting the lumber planks in a direction perpendicular to a lengthwise direction of the lumber planks; said vision unit comprising a first vision sub-unit positioned above and at a first predetermined angle relative to a movement axis of the transversal conveyor; and a second vision sub-unit placed below and at a second predetermined angle relative to the movement axis of the transversal conveyor, the inclination angle of the transversal conveyor being of approximately 30±15 decrees relatively to a horizontal axis; said first predetermined angle is an angle of approximately 60±15 degrees and said second predetermined angle is an angle of approximately 120±15 degrees, wherein each vision sub-unit scans an edge and a face of the lumber planks.

15. The grade optimizer according to claim 14, wherein said processing unit comprises an expert system.

16. The grade optimizer according to claim 14, wherein said processing unit allows analyzing data collected by said vision unit, identifying the data, and monitoring operational parameters of the grade optimizer.

17. The grade optimizer according to claim 14, wherein said vision unit is anchored on the frame.

18. The grade optimizer for lumber planks according to claim 14, wherein said grade optimizer allows treatment of the lumber planks of a length up to 24 feet, at a rate of at least 200 lumber planks per minute with a margin of error of at most 2%.

19. A method for classification of a three-dimensional object moved in a direction perpendicular to a lengthwise direction thereof by a transversal conveyor, comprising:
providing a first vision unit positioned above the transversal conveyor at a first angle relatively to a movement axis of the transversal conveyor;
providing a second vision unit positioned under the transversal conveyor at a second angle relatively to the movement axis of the transversal conveyor, the second vision unit comprising cleaning means;
providing a measuring means connected to the first and to the second vision units; and
acquiring and processing data obtained by the measuring means;
wherein the first vision unit scans a first face and a first edge of the object while the second vision unit scans a second face and a second edge of the object.

20. The method according to claim 19, wherein said providing a first vision unit comprises providing a first vision unit positioned above the transversal conveyor at an angle of approximately 60±15 degrees relatively to the movement axis of the transversal conveyor; and said providing a second vision unit comprises providing a second vision unit positioned under the transversal conveyor at an angle of approximately 120±15 degrees relative to the movement axis of the transversal conveyor.

21. The method according to claim 19, wherein said acquiring data comprises examining an upper longitudinal face and a first side longitudinal lateral face of the object by the first vision unit and examining a lower longitudinal face and a second longitudinal lateral face of the object by the second vision unit; and said processing data comprises processing the acquired data by an optimization unit.

22. The method according to claim 19, comprising placing the transversal conveyer at an inclination angle of approximately 30±15 degrees relatively to a horizontal axis.

* * * * *